(12) United States Patent
Nguyenba et al.

(10) Patent No.: US 11,123,076 B2
(45) Date of Patent: Sep. 21, 2021

(54) MULTI-BAND RUBBER BAND LIGATION DEVICE AND METHOD OF OPERATION THEREOF

(71) Applicant: Logan Medical Devices, Inc., Dallas, TX (US)

(72) Inventors: Andrew Nguyenba, Dallas, TX (US); Alex Lara-Arvizu, Dallas, TX (US); Aron Torres, Dallas, TX (US); Jose R. Rodriguez, Dallas, TX (US); Jesse Grant, Dallas, TX (US); Kyle Sii-Kai Lo, Dallas, TX (US); Lilian Zhan, Dallas, TX (US); Dennis I. Robbins, Dallas, TX (US)

(73) Assignee: Logan Medical Devices, Inc., Dallas, TX (US)

( * ) Notice: Subject to any disclaimer, the term of this patent is extended or adjusted under 35 U.S.C. 154(b) by 224 days.

(21) Appl. No.: 16/395,752

(22) Filed: Apr. 26, 2019

(65) Prior Publication Data
US 2019/0328397 A1 Oct. 31, 2019

Related U.S. Application Data

(60) Provisional application No. 62/663,128, filed on Apr. 26, 2018.

(51) Int. Cl.
*A61B 17/12* (2006.01)
*A61B 17/34* (2006.01)

(52) U.S. Cl.
CPC .......... *A61B 17/12009* (2013.01); *A61B 2017/12018* (2013.01); *A61B 2017/3452* (2013.01); *A61M 2210/1067* (2013.01)

(58) Field of Classification Search
CPC ........ A61B 17/12009; A61B 17/12013; A61B 2017/12018; A61B 2017/3452
See application file for complete search history.

(56) References Cited

U.S. PATENT DOCUMENTS

| 2008/0108871 A1* | 5/2008 | Mohr ................ A61B 17/4208 600/114 |
| 2008/0287965 A1* | 11/2008 | Ducharme ....... A61B 17/12013 606/140 |

* cited by examiner

*Primary Examiner* — Melanie R Tyson
(74) *Attorney, Agent, or Firm* — Ferguson Braswell Fraser Kubasta PC (57) ABSTRACT

A rectal injection device and a method of operating the same. In one embodiment, the device includes: (1) a body having a handle, (2) a suction system associated with the body, (3) a trigger associated with the handle, (4) a pod coupled to the body via a neck and (5) multiple suction ports associated with the pod, each of the multiple suction ports configured to receive a ligation band thereabout, the suction system configured to provide a suction to the multiple suction ports to draw tissue thereinto, the pod configured to deploy the ligation bands upon activation of the trigger.

9 Claims, 8 Drawing Sheets

MULTI-BAND RUBBER BAND LIGATION DEVICE AND METHOD OF OPERATION THEREOF

CROSS-REFERENCE TO RELATED APPLICATION

This application claims priority based on U.S. Provisional Patent Application Ser. No. 62/663,128, filed by Nguyenba, et al., on Apr. 26, 2018, entitled "Shotgun Ligation Device and Method of Operation Thereof," and incorporated herein by reference in its entirety.

TECHNICAL FIELD

This application is directed, in general, to a lower gastrointestinal (GI) medical device and, more specifically, to a multi-band (i.e. "shotgun") ligation device and a method of operating the same.

BACKGROUND

Hemorrhoids are swollen blood vessels located in the rectum and are categorized as internal hemorrhoids or external hemorrhoids. External hemorrhoids are located outside of the body at the anus. Internal hemorrhoids originate within the body, and are characterized into four grades, which are dependent on how much they protrude from the rectum, or prolapse:

Grade I—do not prolapse;
Grade II—prolapse but spontaneously retract into body (reduce);
Grade III—prolapse and must be manually reduced; and
Grade IV—prolapse and cannot be reduced.

As those skilled in the pertinent art are aware, the dentate line, for purposes of this discussion, denotes the boundary between tissue that is innervated with sensory nerve endings and tissue that is not innervated with sensory nerve endings. Internal hemorrhoids which originate above the dentate are not innervated, so physical interaction with the hemorrhoid does not usually cause the patient pain. External hemorrhoids are innervated, and can be painful when touched. This project focuses only on the treatment of internal hemorrhoids.

It is estimated that half of the US population over the age of 50 have suffered from hemorrhoids. Over time, hemorrhoids occur when chronic pooling of blood in the rectum is combined with high internal pressures, such as during excessive straining during bowel movements, obesity, pregnancy, heavy lifting, and a sedentary lifestyle; hemorrhoid prevalence also increases with age. Treating hemorrhoids is a billion-dollar business: 12 in 1000 doctor visits involve hemorrhoids. Hemorrhoids are easiest to treat when they are grades I or II.

Current hemorrhoid treatments range from symptom control, such as creams or home remedies, to curative treatments, which decrease the size of or remove the hemorrhoids altogether. All conventional curative treatments are invasive procedures and require the administration of a specialized clinician. The treatments involve: (1) removing the hemorrhoid, such as in hemorrhoidectomy, or (2) truncating blood flow to the hemorrhoid by causing scar tissue to form. The latter type ultimately reduces the size of the treated hemorrhoid. These procedures may require multiple visits, or are lengthy procedures for patients, or both, and are usually performed by a GI specialist; they include the following:

rubber band ligation (RBL)—application of rubber bands on or near internal hemorrhoids;
infrared coagulation therapy—use of infrared light to clot off hemorrhoidal vessels;
ultroid treatment—application of a direct electrical current to the hemorrhoid; and
sclerotherapy—use of chemical injection, usually in four quadrants, to scar and shrink hemorrhoids.

RBL is a curative and preventative procedure that applies rubber bands on or near internal hemorrhoids. The RBL procedure has two major phases of operation: tissue capture and band deployment.

Tissue capture has traditionally been accomplished with a grasping instrument. Current RBL procedures use suction from either a syringe or a medical grade suction device to draw in the tissue of interest, which reduces the possibility of its rupturing. The tissue of interest may be the hemorrhoid itself or the mucosa near the hemorrhoid, the lining of the rectum. Next, the rubber band from the ligator is displaced onto the tissue of interest. When the tissue captured by the ligation band atrophies, a dime-sized scar forms and occludes blood flow to nearby vessels, which causes the hemorrhoid to reduce in size. Depending on the device used, an RBL procedure may or may not require visualization for band deployment, as will now be discussed. It is of note that the treatment's flexibility to ligate tissue near the hemorrhoid, rather than to ligate the hemorrhoid directly, is a recent development known by a handful of specialized GI practitioners; most ligation band devices are marketed with the intent of applying the band directly to the hemorrhoid.

Conventional RBL treatment is often employed using the CRH O'Regan System®, which allows clinicians to deliver ligation bands one at a time without visualization. Suction from the O'Regan system is accomplished with a syringe barrel and plunger. It is because the clinician can feel that tissue was successfully captured through resistance from the plunger that allows the O'Regan system not to require visualization. The O'Regan system must be intermittently cleaned and reloaded with a new ligation band between band deployments. This procedure is cumbersome considering the size of the bands, the clinician's hands being gloved, and possible traces of lubricant used for device insertion, making it difficult to load bands onto the device.

An alternative device currently available on the market is the Short Shot® Saeed Hemorrhoidal Multi-Band Ligator System. The Short Shot® system has four bands preloaded onto the barrel of the device, called the drum, for deployment. This removes the need for reloading. Producing suction is not integrated into the Short Shot® system and must be achieved from a separate constant vacuum source. Visualization is required to verify tissue capture and is accomplished via anoscope and a separate illumination source, allowing the Short Shot® system to be repositioned for each band ligation placement. The Short Shot® system does not supply illumination.

Although the Short Shot® system removes the need for loading bands between tissue ligation, the need for visualization, illumination, and a separate suction source are drawbacks to the system. The O'Regan system does not require visualization, but is cumbersome in that the clinician needs to reload bands between band deployments.

SUMMARY

One aspect provides a rectal injection device and a method of operating the same. In one embodiment, the device includes: (1) a body having a handle, (2) a suction system associated with the body, (3) a trigger associated with the handle, (4) a pod coupled to the body via a neck and (5) multiple suction ports associated with the pod, each of the multiple suction ports configured to receive a ligation band thereabout, the suction system configured to provide a suction to the multiple suction ports to draw tissue thereinto, the pod configured to deploy the ligation bands upon activation of the trigger.

Another aspect provides a method of operating a rectal injection device. In one embodiment, the method includes: (1) loading ligation bands about suction ports in a pod of the device, (2) inserting the pod into a rectum of a subject, (3) actuating a suction through the suction ports, the suction drawing tissue of the rectum into the suction ports and (4) actuating a trigger of the device to cause the ligation bands to be deployed about the tissue.

BRIEF DESCRIPTION OF THE DRAWINGS

Reference is now made to the following descriptions taken in conjunction with the accompanying drawings, in which.

DETAILED DESCRIPTION

Introduced herein are various embodiments of an RBL device that would (1) automate the deployment of multiple ligation bands and (2) not require visualization for the procedure.

In certain embodiments, the ligation device would require less specialization for operation, allowing long-lasting hemorrhoid treatment to even be delivered by general practitioners. This would, in turn, increase the number of physicians willing to use such devices and increase patient access to hemorrhoid treatments. Certain embodiments of this device may be used with one or more sclerotherapy devices, allowing clinicians to increase the grade of hemorrhoids that are treatable with band ligation therapy.

Some embodiments of the RBL device have the following features: (1) the ability to automate the deployment of three, or a plurality, of ligation bands, (2) the ability to provide an indication that it is inserted at an appropriate depth into the patient, guaranteeing placement of ligation bands above the anal dentate line, (3) the ability to deploy the ligation bands at 120° intervals around the circumference of the rectum, specifically: the left lateral region, the right anterior region, and the right posterior region, (4) the ability to operate without visualization, (5) the ability to produce a suitable amount of suction from an internal source. (6) The ability to place ligation bands on the tissue so they remain after the procedure, and (7) the ability to be easy to use, so that non-specialized clinicians can operate the device. Various embodiments are configured to place ligation bands concurrently or sequentially. Other embodiments differ in terms of the number of ligation bands they can deploy sequentially or concurrently, and in other respects.

Some embodiments of the RBL device have the following features: (1) device dimensions comparable to those of current systems: a suction port inner diameter of 8.9 mm, a suction port minimum outer diameter of 11.6 mm, a suction port outer diameter at an indication notch of 15.7 mm, a suction port maximum outer diameter of 18.8 mm, and a maximum insertion length of device of 100 mm, (2) an insertable diameter that does not exceed 30 mm, (3) materials that are biocompatible with rectal physiology, and (4) non-reusable portions that are manufacturable via low-cost methods, such as injection molding.

As stated above, two groups of embodiments are configured to place ligation bands concurrently or sequentially. The first group (concurrent band deployment embodiments), requires a suction port for each band so that the bands can be deployed at the same time. The second group (sequential band deployment embodiments), requires only one suction port, but requires a rotation mechanism to move the suction port to each band or each band to the suction port.

Figure 1:
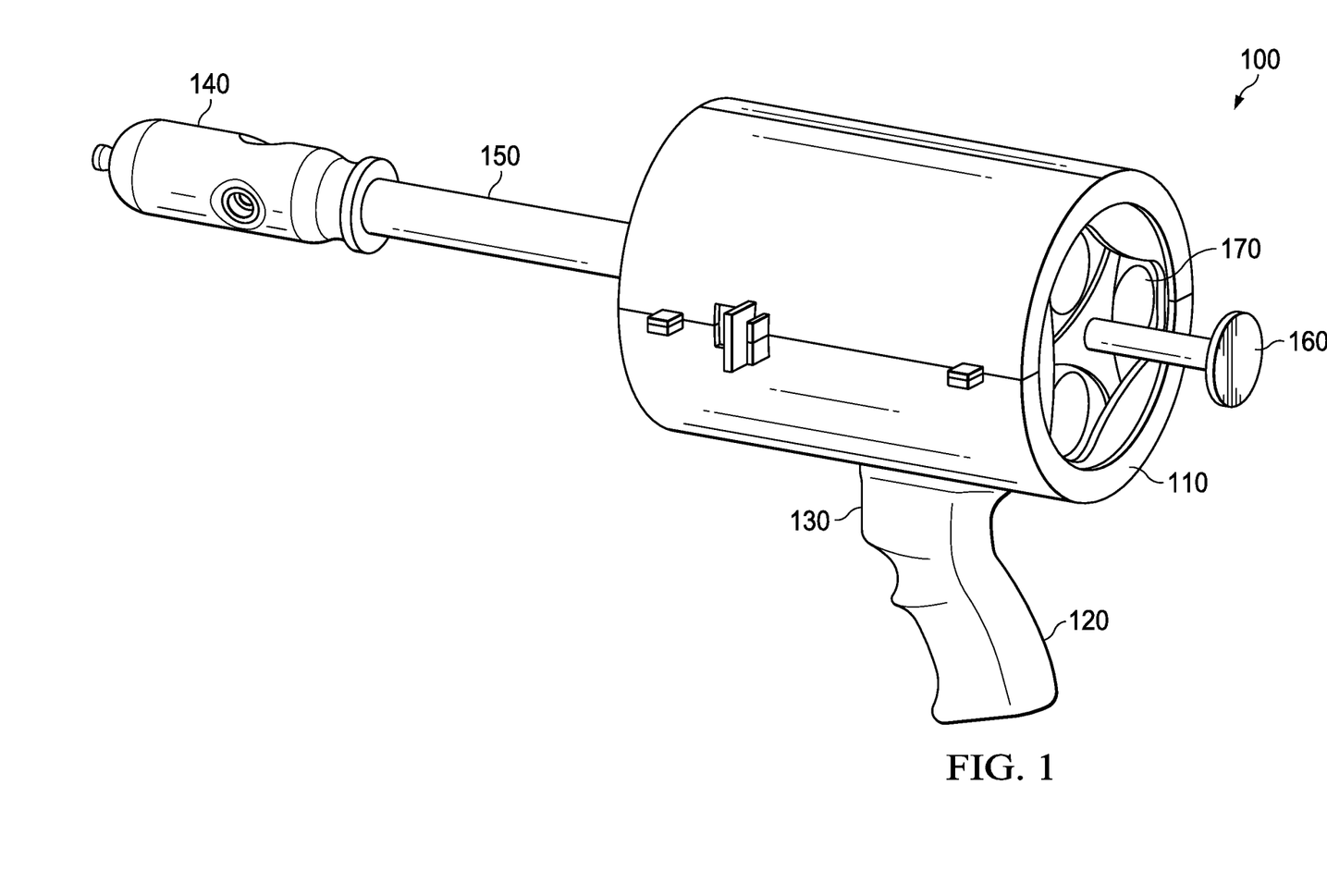
FIG. 1 is an isometric view of one embodiment of a multi-band ligation device.

FIG. 1 is an isometric view of one embodiment of a multi-band ligation device 100. The device 100 includes a body 110. The body 110 is connected to a handle 120 that includes a trigger 130. The body 110 is further connected to a pod 140 via a neck 150. The body 110 further contains a suction system that, in the illustrated embodiment, includes a coupler 160 and syringe cavities 170. The syringe cavities 170 are configured to receive syringes (not shown) employable to draw a suction through unreferenced suction ports in the pod 140. In an alternative embodiment, the suction system includes a receptacle to receive an external suction tube.

To operate the device 100, syringes (not shown in FIG. 1) are placed in the cavities 170, and ligation bands (not shown) are loaded about the suction ports (not referenced) in the pod 140. The pod 140 is then inserted into the rectum (not shown) of a subject. The coupler 160 is then actuated by being drawn away from the body 110, causing the syringes to draw a suction through the suction ports, drawing tissue into the suction ports. The trigger 130 is then pulled, causing the ligation bands to be deployed about the tissue. The trigger 130 is then released and the device 100 withdrawn from the rectum of the subject.

Figure 2A:
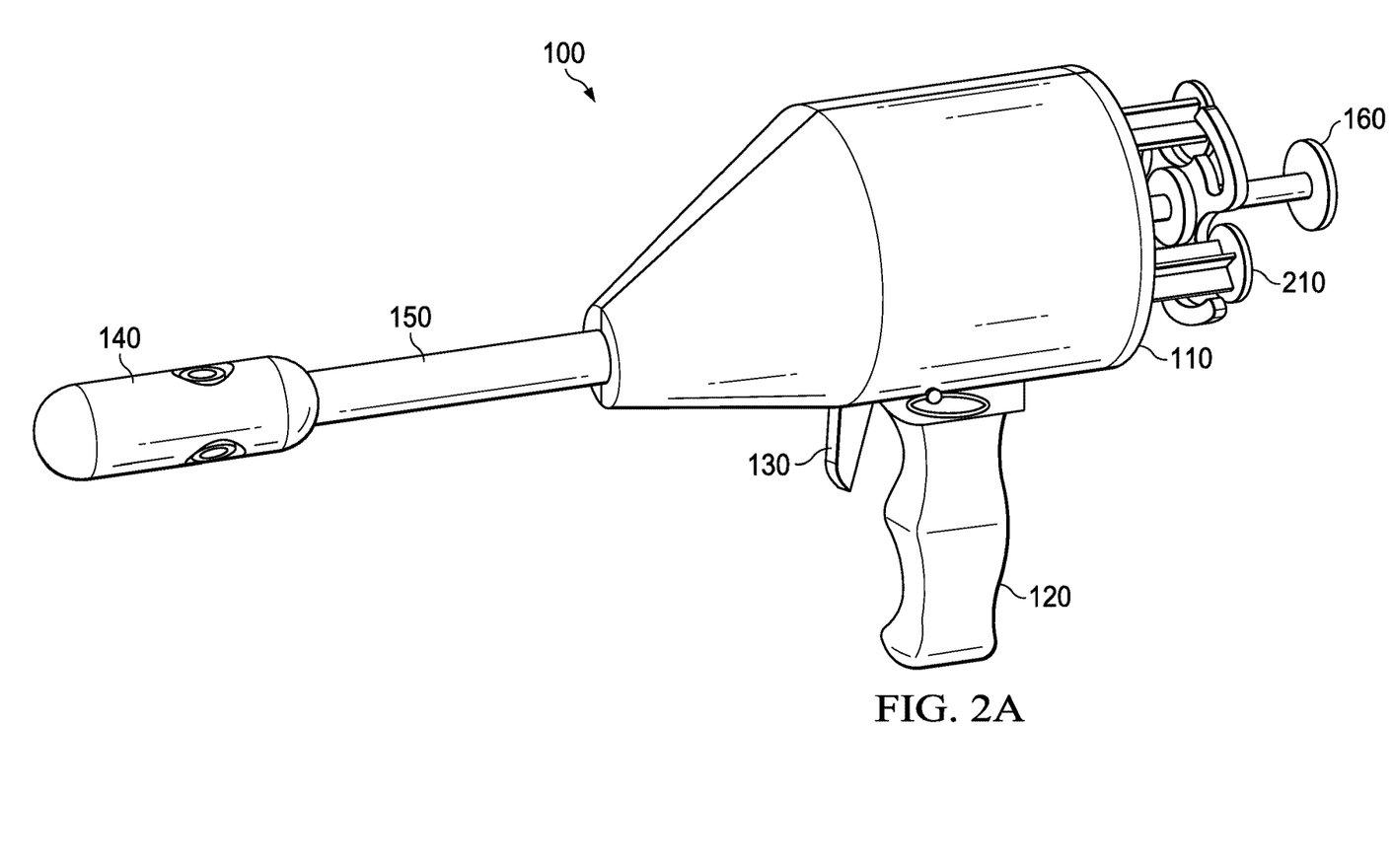
FIG. 2A is an isometric view of another embodiment of the multi-band ligation device.

FIG. 2A is an isometric view of another embodiment of the multi-band ligation device. The embodiment of FIG. 2A differs from that of FIG. 1 in the shape of the body 110 and the placement of the trigger 130. It will be noted that the body 110 of FIG. 2A is tapered proximate the neck 150. It will also be noted that the trigger 130 of FIG. 2A is connected directly to the body 110 instead of the handle 120. Still, the trigger 130 is associated with the handle 120. FIG. 2A also shows syringes (one of which being referenced as 210) situated in the cavities (unreferenced in FIG. 2A). Finally, FIG. 2A shows additional detail in the coupler 160, namely that it includes a flange (unreferenced) that engages plungers (unreferenced) of the syringes, allowing actuation of the coupler 160 to result in a simultaneous drawing back of the plungers.

Figure 2B:
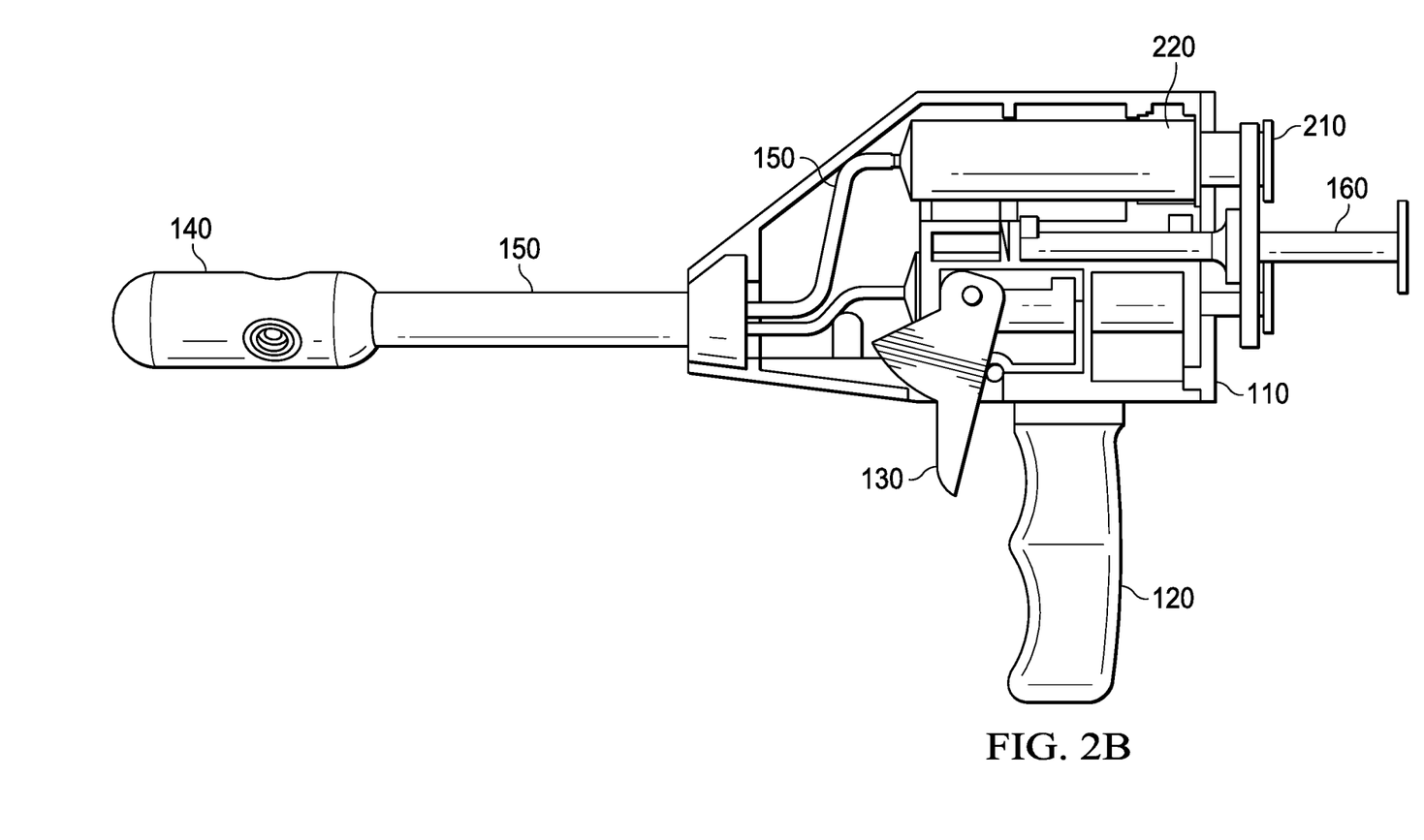
FIG. 2B is an isometric sectional view of an internal components in the pod of the embodiment of FIG. 2A.

FIG. 2B is an isometric sectional view of an internal components in the pod of the embodiment of FIG. 2A. FIG. 2A shows more of the syringes (one of which now being referenced as 220) and tubing 150 connecting the syringes 220 to the suction ports (unreferenced) through the neck 150 for air communication therebetween. FIG. 2A further shows a linkage (unreferenced) that couples the trigger 130 to the pod 140 through the neck 150, allowing the trigger to move petals (unreferenced) of the pod 140 to deploy the ligation bands (not shown).

In one embodiment, the suction system is comprised of VacLokm syringes. The VacLokm syringes were chosen over other similar syringes because the plunger could be locked in place to maintain suction. In an alternative embodiment, a suction source, such as may be available on a wall outlet, may be coupled by a tube to the device 100, obviating a need for the coupler 160 and the syringes.

Figure 3:
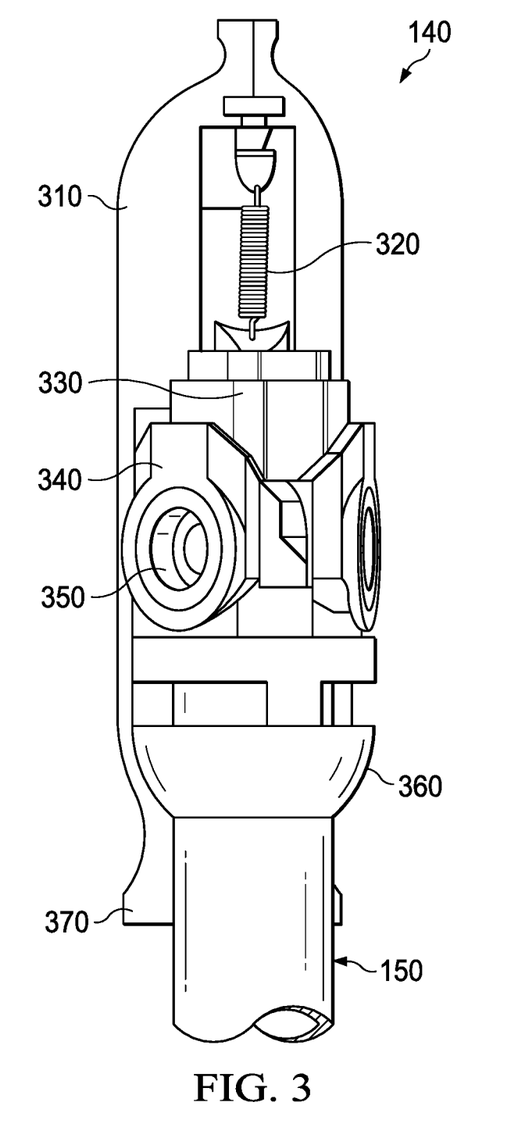
FIG. 3 is an internal, detailed view of pod and neck components of the embodiment of FIGS. 2A and 2B.

FIG. 3 is an internal, detailed view of pod 140 and neck 150 components of the embodiment of FIGS. 2A and 2B. Shown are a petal 310 (one of three petals in the embodiment of FIG. 3), a spring 320 configured to bias the petals 310 toward a closed position, a wedge 330 configured to urge a ring 340 to expand, urging the petals 310 toward an open position when the force of the spring 320 is overcome, a transition 360 configured to provide a reduction in diameter for the neck 150 and a flange 370 configured to discourage over-insertion of the pod 140 into the rectum (not shown). Actuation of the trigger of FIG. 1, 2A or 2B causes the force of the spring 320 to be overcome and the wedge 330 to bear against the petals 310, causing the petals 310 to open, causing ligation bands (not shown) surrounding the suction ports 350 to deploy about tissue (not shown) drawn into the suction ports 350.

In one embodiment, the linkage takes the form of a monofilament line connecting the wedge to the trigger. Movement of the monofilament line moves the wedge and pushes the ring radially outwards. The ligation bands, which are positioned about the suction ports in front of each of the rings, are moved off the suction port and around the captured tissue. The syringes are then returned to their original position to release the vacuum and the device is removed.

Figure 4:
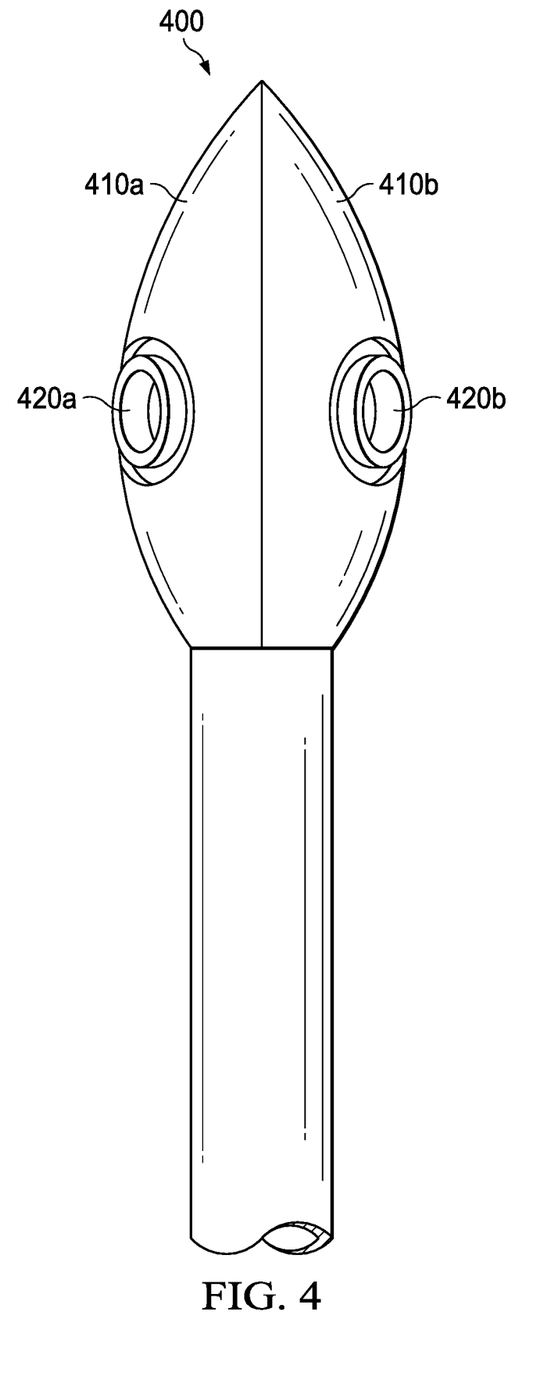
FIG. 4 is an isometric view of a pod portion of a multi-band RBL device in which suction ports retract to deploy ligation bands.
Figure 5:
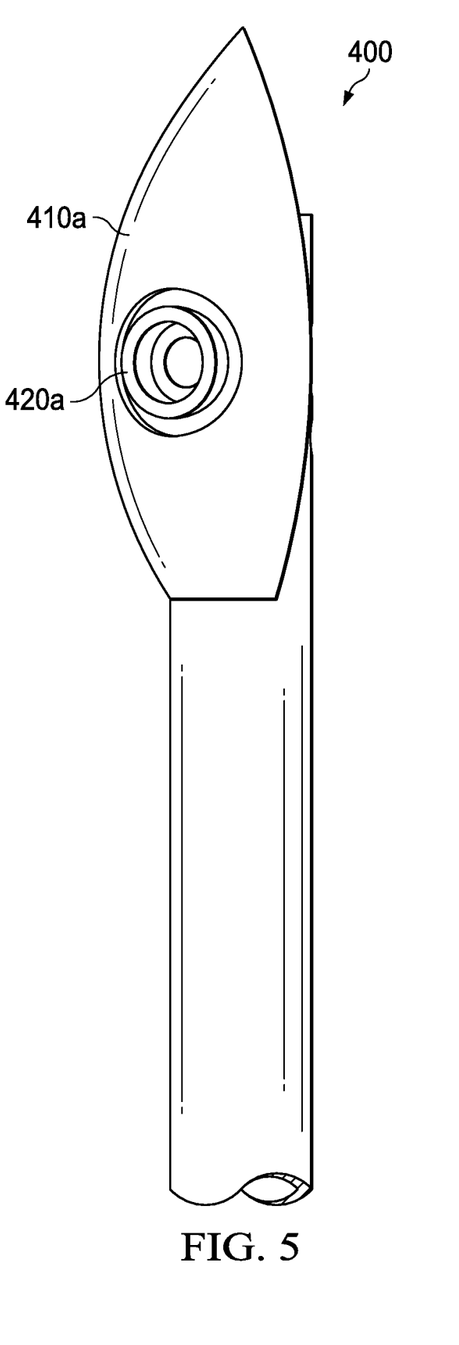
FIG. 5 is a sectional isometric view of one petal piece of the multi-band RBL device embodiment of FIG. 4.

FIGS. 4 and 5 are isometric and sectional isometric views of a pod embodiment 400 with fixed petals and movable suction ports that operates under a concurrent band deployment mechanism. Three modular petals (two of which being referenced as 410a, 410b) sit flush with each other, creating the tip of the device, and each petal-shaped piece contains a suction port (two of which being referenced as 420a, 420b) with tubing (not shown) inside. Though the petal shapes differ from those of the embodiment of FIGS. 1-3, they serve to illustrate how ligation bands may be secured about suction ports.

Figure 6:
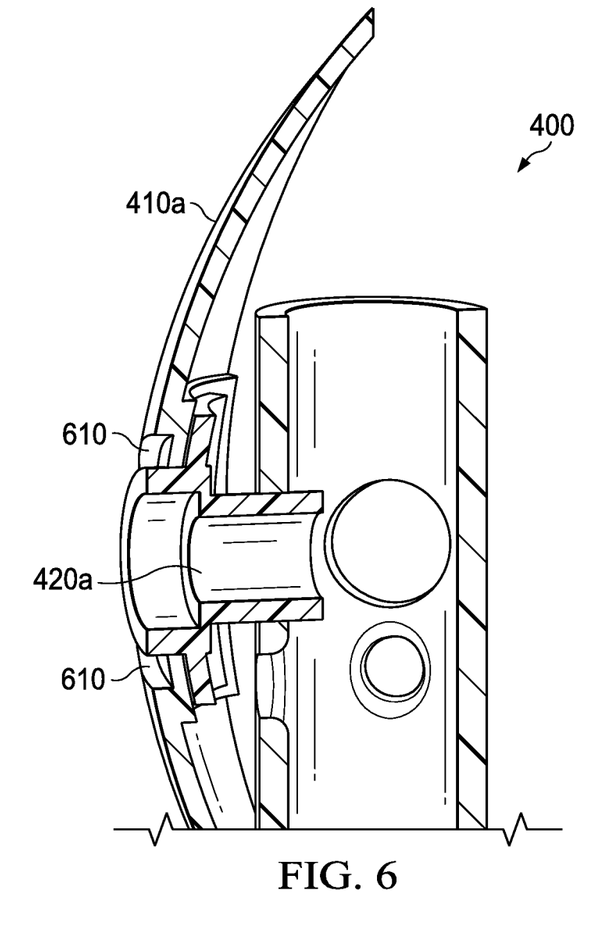
FIG. 6 is a more detailed, cutaway view of the petal piece of FIG. 5 showing recessed grooves into which a ligation band may be pre-loaded.
Figure 7:
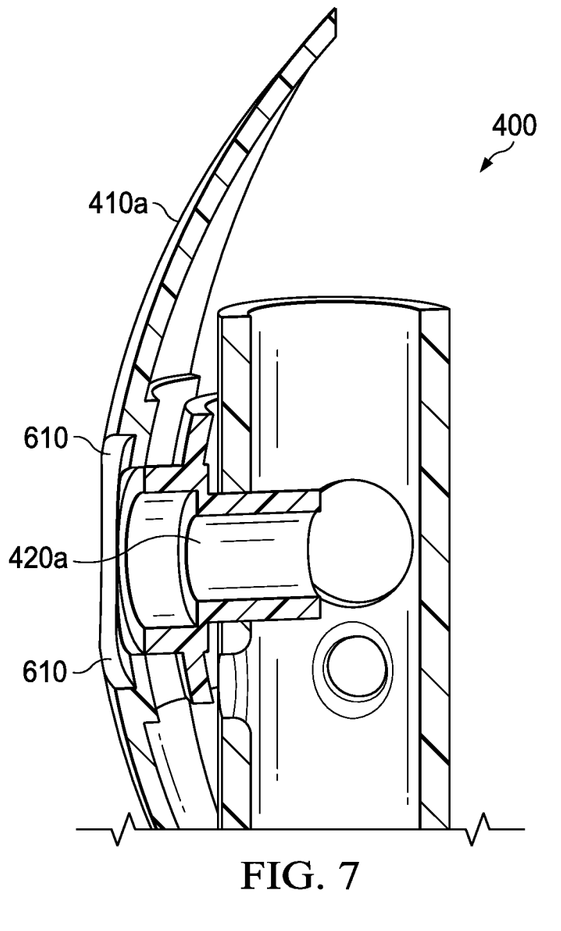
FIG. 7 is the same cutaway view of FIG. 6 in which a suction port is retracted to effect deployment of the ligation band.
Figure 8:
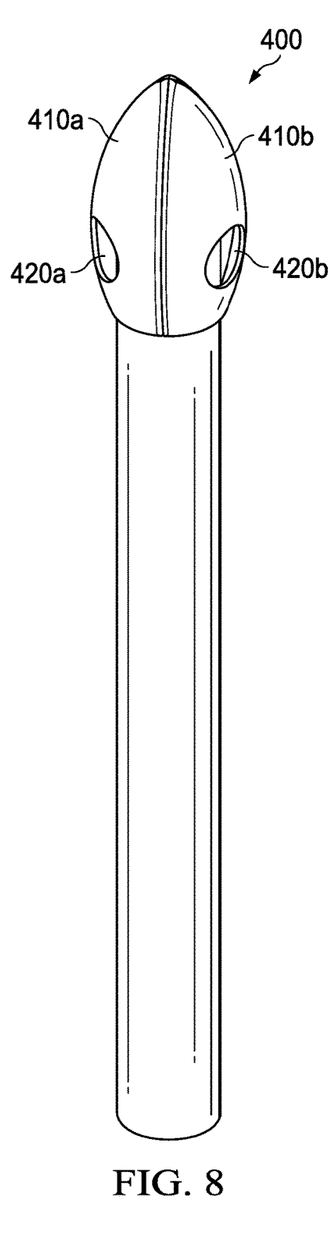
FIG. 8 is an isometric view of a pod portion of a multi-band RBL device in which petal pieces spread to deploy the ligation bands.

FIGS. 6 and 7 depict the band deployment mechanism in more detail. A band (not shown) is preloaded into each recessed groove (one being designated 610). The suction port 420a is then retracted using a trigger mechanism (not shown), as shown in FIG. 8. Retraction of the suction port 420a causes the petals 410a to push the preloaded bands off the suction port 420a and onto the captured tissue.

Figure 9:
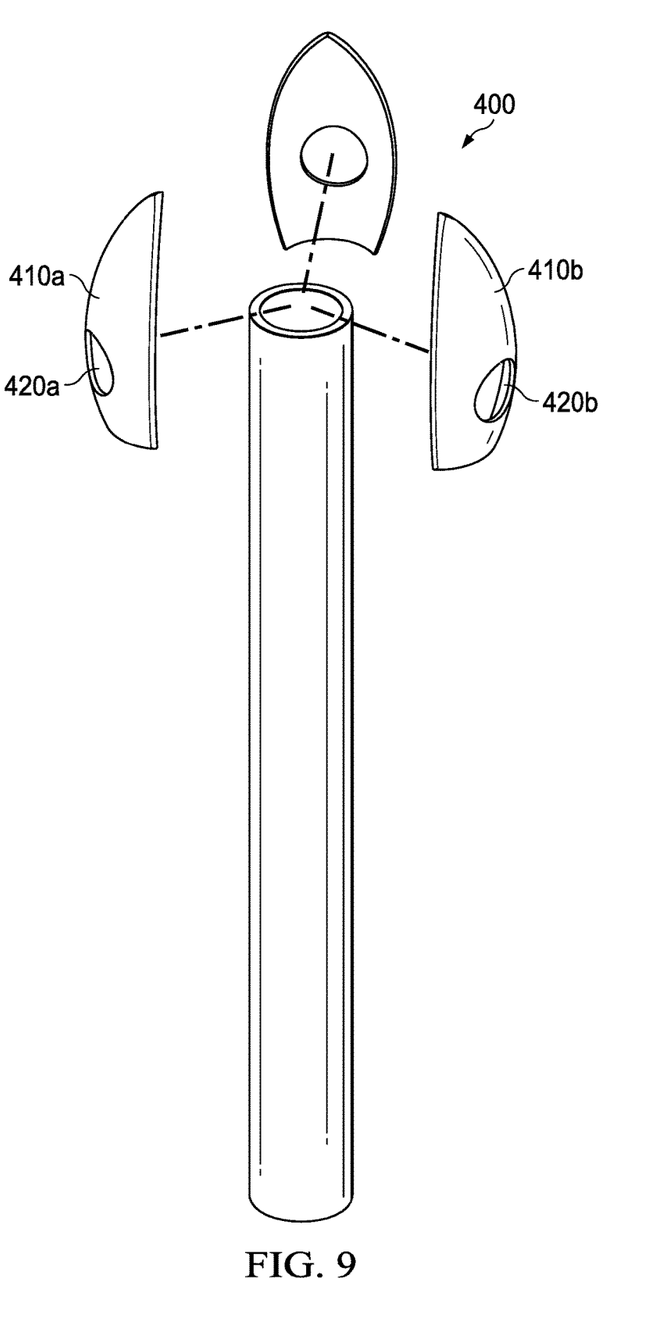
FIG. 9 is the same isometric view of FIG. 8 in which the petal pieces have been spread to deploy the ligation bands.

FIGS. 8 and 9 depict a pod embodiment with movable petals and fixed suction ports. In a closed state, seen in FIG. 8, the suction ports 420a, 420b are configured to capture the rectal wall tissue (not shown) using a suction generation mechanism (not shown). Once sufficient tissue (not shown) is captured, the device 400 is triggered to enter a deployed state seen in FIG. 9, and bands are pushed off the suction tube (not pictured) and onto the tissue by the outward movement of the petals 420a, 420b.

Figure 10:
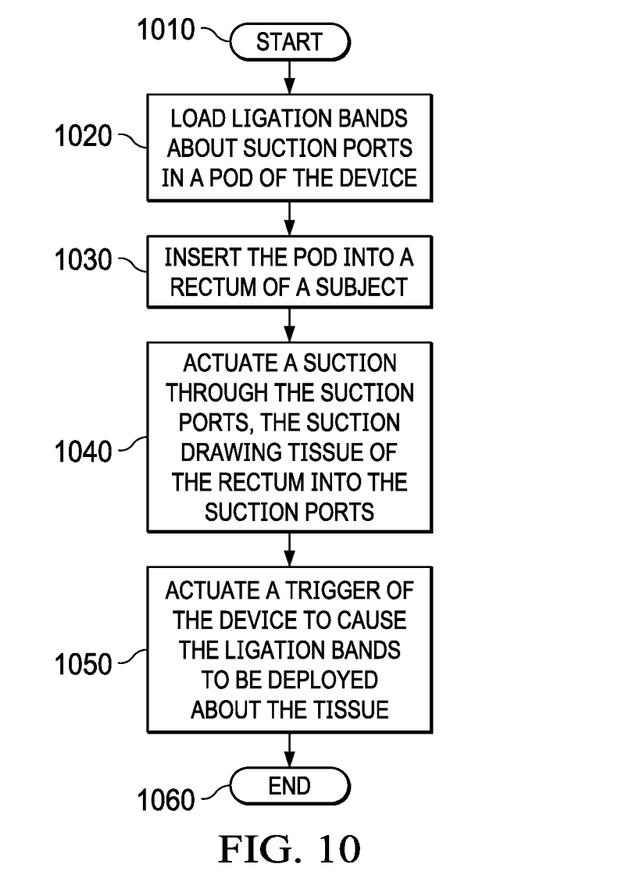
FIG. 10 is a flow diagram of one embodiment of a method of using a multi-band RBL device.

FIG. 10 is a flow diagram of one embodiment of a method of using a multi-band RBL device. The method begins in a start step 1010, when syringes are placed in cavities of the device. In a step 1020, ligation bands are loaded about the suction ports in a pod of the device. In a step 1030, the pod is inserted into the rectum of a subject. In a step 1040, suction is actuated through the suction ports, perhaps by drawing a coupler away from a body of the device. This causes tissue to be drawn into the suction ports. In a step 1050, a trigger of the device is actuated, causing the ligation bands to be deployed about the tissue. The trigger may then be released, and the pod withdrawn from the rectum of the subject. The method ends in an end step 1080.

Those skilled in the art to which this application relates will appreciate that other and further additions, deletions, substitutions and modifications may be made to the described embodiments.

What is claimed is:

1. A rectal injection device, comprising:
    a body having a handle;
    a suction system associated with said body, said suction system comprising:
        a plurality of cavities in said body configured to receive syringes; and
        a coupler configured to engage plungers of said syringes;
    a trigger associated with said handle;
    a pod coupled to said body via a neck; and
    multiple suction ports associated with said pod, each of said multiple suction ports configured to receive a ligation band thereabout, said suction system configured to provide a suction to said multiple suction ports to draw tissue thereinto, said pod configured to deploy said ligation bands upon activation of said trigger.

2. The device as recited in claim 1 wherein said body is tapered proximate said neck.

3. The device as recited in claim 1 wherein said trigger is directly connected to said body.

4. The device as recited in claim 1 wherein said pod comprises a plurality of petals having recesses about said suction ports configured to receive said ligation bands.

5. The device as recited in claim 4 wherein said trigger is configured to move said plurality of petals to deploy said ligation bands.

6. The device as recited in claim 4 wherein said trigger is configured to move said suction ports to deploy said ligation bands.

7. The device as recited in claim 4 wherein said plurality of petals comprises three petals.

8. The device as recited in claim 1 wherein said multiple suction ports comprise three suction ports.

9. The device as recited in claim 1 wherein said pod comprises a flange.

* * * * *